United States Patent
Mavroeidis et al.

(10) Patent No.: US 12,201,443 B2
(45) Date of Patent: Jan. 21, 2025

(54) DETERMINING A SLEEP STATE OF A USER

(71) Applicant: KONINKLIJKE PHILIPS N.V., Eindhoven (NL)

(72) Inventors: Dimitrios Mavroeidis, Utrecht (NL); Ulf Grossekathoefer, Eindhoven (NL); Aki Sakari Härmä, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 119 days.

(21) Appl. No.: 17/549,293

(22) Filed: Dec. 13, 2021

(65) Prior Publication Data

US 2022/0183620 A1 Jun. 16, 2022

(30) Foreign Application Priority Data

Dec. 14, 2020 (EP) .................................. 20213750

(51) Int. Cl.
*A61B 5/00* (2006.01)
*A61B 5/38* (2021.01)

(52) U.S. Cl.
CPC ............. *A61B 5/4812* (2013.01); *A61B 5/38* (2021.01); *A61B 5/4809* (2013.01); *A61B 5/7221* (2013.01); *A61B 5/7267* (2013.01)

(58) Field of Classification Search
None
See application file for complete search history.

(56) References Cited

U.S. PATENT DOCUMENTS

2006/0070451 A1* 4/2006 Walsh ............... G01B 7/22
73/780
2008/0033304 A1* 2/2008 Dalal ................ A61B 5/4812
600/529

(Continued)

FOREIGN PATENT DOCUMENTS

WO 2002100267 A1 12/2002
WO 2015006364 A2 1/2015
WO WO-2022074626 A1 * 4/2022 ........ A61M 16/0069

OTHER PUBLICATIONS

H.-V. V Ngo, A. Miedema, I. Faude, T. Martinetz, M. Molle, and J. Born, "Driving Sleep Slow Oscillations by Auditory Closed-Loop Stimulation-A Self-Limiting Process," J. Neurosci., vol. 35, No. 17, pp. 6630-6638, 2015.

(Continued)

*Primary Examiner* — Devin B Henson
*Assistant Examiner* — Matthew Eric Ogles
(74) *Attorney, Agent, or Firm* — Michael W. Haas

(57) ABSTRACT

According to an embodiment of an aspect, there is provided a computer-implemented method for determining a sleep state of a user. The method comprising receiving (S11) a physiological signal from a physiological signal detector used by the user. The method further comprising determining (S12), based on the received physiological signal, the sleep state of the user. The method further comprising calculating (S13) a reliability value associated with the determination. The reliability value being calculated based on a comparison of the received physiological signal with historic physiological signals of the same sleep state as the determined sleep state. There is further provided a device (20) and computer-readable medium (30). In accordance (Continued)

with the present disclosure, the sleep state of a user may be determined with greater accuracy when compared with past methods.

6 Claims, 5 Drawing Sheets

(56) References Cited

U.S. PATENT DOCUMENTS

| | | | | |
|---|---|---|---|---|
| 2010/0076333 | A9* | 3/2010 | Burton | A61B 5/318 600/595 |
| 2014/0276242 | A1* | 9/2014 | Chen | A61B 5/1116 600/595 |
| 2015/0190086 | A1* | 7/2015 | Chan | A61B 5/4812 600/300 |
| 2016/0058298 | A1* | 3/2016 | Koch | G01K 13/20 600/549 |
| 2017/0259428 | A1* | 9/2017 | Assad | G16H 40/67 |
| 2017/0278195 | A1 | 9/2017 | Washio | |
| 2019/0110755 | A1* | 4/2019 | Capodilupo | A61B 5/02055 |
| 2019/0282152 | A1* | 9/2019 | Ouwerkerk | A61B 5/681 |
| 2020/0205704 | A1 | 7/2020 | Bhavaraju | |

OTHER PUBLICATIONS

M. Bellesi, B. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.

N. A. Papalambros, G. Santostasi, R. G. Malkani, R. Braun, S. Weintraub, K. A. Paller, and P. C. Zee, "Acoustic enhancement of sleep slow oscillations and concomitant memory improvement in older adults," Front. Hum. Neurosci., vol. 11, No. March, pp. 1-14, 2017.

M. M. Leminen, J. Virkkala, E. Saure, T. Paajanen, P. C. Zee, and G. Santostasi, "Enhanced Memory Consolidation via Automatic Sound Stimulation During Non-REM Sleep," Sleep, vol. 40, No. 3, pp. 1-10, 2017.

B. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.

H. H. Jasper, "The ten-twenty electrode system of the international federation," Electroencephalogr. Clin. Neurophysiol., vol. 10, No. 1, pp. 371-375, 1958.

Liang, S. et al., "Enhancing The Reliability of Out-of-distribution Image Detection in Neural Networks", https://arxiv.org/abs/1706.02690, Aug. 2020.

* cited by examiner

DETERMINING A SLEEP STATE OF A USER

CROSS-REFERENCE TO PRIOR APPLICATIONS

This application claims the benefit of European Patent Application No. 20213750.1, filed on 14 Dec. 2020. This application is hereby incorporated by reference herein.

FIELD

The present invention relates to determining a sleep state of a user. The determining may be associated with analysis of physiological readings taken from the user.

DESCRIPTION OF THE RELATED ART

Systems for monitoring sleep and delivering sensory stimulation to users during sleep may include physiological sensor-based sleep monitoring, such as polysomnogram (PSG), electroencephalogram (EEG), or electrocardiogram (ECG) sensor-based sleep monitoring. Such a system may be state-based, meaning stimulation is delivered responsive to physiological parameters indicating a sleep state of the user. Sleep states may include sleeping and waking (or being awake). Sleep may be categorized into either REM (rapid eye movement) sleep or NREM (non-rapid eye movement) sleep. NREM sleep may be split into different "stages", such as stage 1, stage 2 and stage 3, relating to progressively more "deep" sleep. Stage 3 NREM sleep is a deep form of sleep and one of the sleep states. NREM sleep is known to have beneficial effects on brain function, such as memory. In order to determine whether a person is in stage 3 NREM sleep, physiological measurements may be taken and monitored for characteristics indicative of the different states. Under some conditions however, quality of some measurements may be compromised due to factors such as movement, electrode misplacement or perspiration, which leads to less accurate sleep state determination. Thus, there is a need for a method to improve the accuracy of sleep state determination.

SUMMARY

According to an embodiment of an aspect, there is provided a computer-implemented method for determining a sleep state of a user. The method comprises receiving a physiological signal from a physiological signal detector used by the user. The method further comprises determining, based on the received physiological signal, the sleep state of the user. The method further comprises calculating a reliability value associated with the determination. The reliability value is calculated based on a comparison of the received physiological signal with historic physiological signals of the same sleep state as the determined sleep state.

According to an embodiment of a further aspect, there is provided a device for determining a sleep state of a user. The device comprises a receiver to receive a physiological signal from a physiological signal detector used by the user. The device further comprises a processor to determine, based on the received physiological signal, the sleep state of the user. The processor further calculates a reliability value associated with the determination. The reliability value is calculated based on a comparison of the received physiological signal with historic physiological signals of the same sleep state as the determined sleep state.

According to an embodiment of a further aspect, there is provided a non-transitory computer-readable medium storing a program which, when executed on a computer, is configured to cause the computer to perform a process. The process comprises determining the sleep state of the user based on a received physiological signal received from a physiological signal detector used by a user. The process further comprises calculating a reliability value associated with the determination. The reliability value is calculated based on a comparison of the received physiological signal with historic physiological signals of the same sleep state as the determined sleep state.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
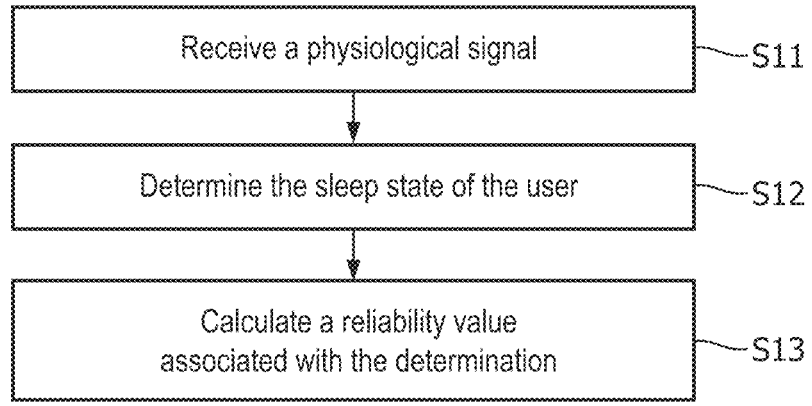
FIG. 1 is a flowchart of an example of a method in accordance with an embodiment.

Embodiments of aspects may provide a method, device and computer-readable medium, as well as a computer program and system, to determine a sleep state of a user.

Sleep states may include sleeping or being awake. Sleep may be categorized into either REM (rapid eye movement) sleep or NREM (non-rapid eye movement) sleep. NREM sleep may be split into different "stages", such as stage 1, stage 2 and stage 3, relating to progressively more "deep" sleep. Each different sleep stage may be indicative of a different sleep state. Categorising sleep into stages based on physiological readings may be carried out manually by an experienced medical professional. Stage 3 NREM sleep is a deep form of sleep. NREM sleep is known to have beneficial effects on brain function, such as improved memory. The restorative value of sleep can be enhanced by auditory stimulation in stage 3 (deep) NREM sleep. In particular, research has shown that auditory stimulation appropriately applied during sleep can enhance slow waves, which are characteristic of stage 3, which in turn enhances the restorative qualities of sleep. Stage 3 sleep may be detected by real-time analysis of physiological measurements from a person, such as PSG, ECG or EEG measurements for example.

Some wearable devices, such as the Philips SmartSleep system, may be used to detect sleep states, in particular stage 3 sleep, and deliver appropriate stimulation while ensuring sleep is not disturbed. Such a system may provide a closed-loop, EEG-based system that may detect deep sleep in real-time and deliver auditory stimulation to enhance sleep slow waves without causing arousal/disturbing the sleep.

In order to determine whether a person is in stage 3 NREM sleep, physiological measurements may be taken and monitored for characteristics indicative of the different states of sleep. Under some conditions however, quality of some physiological measurements may be compromised due to factors such as movement, electrode misplacement or perspiration, which leads to less accurate sleep state detection.

In order to increase the accuracy of stage 3 NREM sleep detection, physiological measurements, such as PSG, ECG or EEG measurements, may be taken over a period of time and analyzed to determine patterns indicating stage 3 NREM sleep. The analysis may initially be performed manually or automatically. Such measurements may be used to train a deep neural network to detect similar patterns in future measurements. In some instances, one category of physiological measurements may be combined with data from other sensors, such as inertia sensors/accelerometers, temperature sensors, strain sensors or skin conductance sensors, to improve the categorization of sleep states.

Some physiological measurements may be of poor quality such that manual categorization of sleep states becomes difficult. A processor, for example on which a deep neural network is implemented, may however be able to categories such sleep states, even when a human annotator cannot. In order to assist the neural network in analyzing physiological measurements and categorizing sleep states, reliability of the measured data may be indicated. EEG measurements are discussed in detail as one example of physiological measurements taken. However, any other physiological measurements may be used, such as electrocardiogram (ECG), polysomnogram (PSG), eye movements (EOG), muscle activity or heart rate.

In an example, as shown in FIG. 1, there is provided an embodiment of a computer-implemented method for determining a sleep state of a user. The method may comprise receiving S11 a physiological signal. The physiological signal may be received from a physiological signal detector used by the user. The method may further comprise determining S12 the sleep state of the user. The determining may be carried out based on the received physiological signal. The method may further comprise calculating S13 a reliability value associated with the determination. The reliability value may be calculated based on a comparison of the received physiological signal with historic physiological signals of the same sleep state as the determined sleep state.

Accurate determination of a sleep state of a user may be desirable to improve the efficacy of therapies, including stimulation of the user, to improve the quality of sleep and therefore increase the beneficial effects on the user. An electroencephalogram (EEG), for example, is seen generally as a reliable method for monitoring the brain activity of a user, from which brain activity the respective sleep states may be identified. In some instances however, such as those mentioned above; movement, electrode misplacement or perspiration, an EEG signal may be affected, such that the respective sleep states become less easy to identify. With the comparison to historic EEG signals, identification of sleep states in such instances may be improved by the method described. A polysomnogram signal may include one or more categories of data normally associated with a polysomnogram, including for example EEG. A polysomnogram signal detector may be any suitable detector to detect the one or more categories of data normally associated with a polysomnogram. A physiological signal may include one or more categories of data related to the physiology of the user, including for example PSG, EEG and/or ECG data. Physiological signals may be data representative of physiological readings taken by any suitable sensor, such as a physiological signal detector. Physiological signals may be received directly or indirectly from the physiological signal detector.

Historic physiological signals, including EEG signals for example, may include physiological signals that have previously had the sleep state of the user determined. This determination may have been carried out manually or automatically. The historic physiological signals may relate to the same user or may relate to multiple users. Historic physiological signals may also have an associated reliability value and physiological signals below a threshold reliability value may be excluded from the comparison or excluded from the historic signals. Physiological signals may for example be direct outputs from physiological sensors or may be data relating to or indicative of physiological readings. For EEG signals, these may for example be direct outputs from an EEG or may be data relating to or indicative of EEG readings. Comparison between physiological signals and historic physiological signals may be performed on the same type of signals, such as comparing EEG signals with historic EEG signals.

The reliability value may be calculated on the basis of how far from historic signal data the received signals lie. That is to say, for EEG signals for example, each sleep state may for example have characteristic EEG patterns, such as wavelength and period of time between the start and the end of the sleep state. Large deviations in such characteristics may lead to a higher level of uncertainty regarding the classification of the sleep state and therefore a lower reliability value. If the EEG signals lie within an expected wavelength range and period length range, then the uncertainty regarding the classification of the sleep state is low and therefore a higher reliability value may be calculated.

Further possible sources of inaccuracies in EEG signals, for example, may include any one or more of:

Misplacement of electrodes. An EEG, for example, may be detected by placing electrodes at specific points on the user's skin. If the electrodes are incorrectly connected to the head of the user, the EEG readings may be affected. This may be due to user error or sometimes may be the result of an unusual head shape. In some examples, the electrodes may be part of a "wearable" device, such as a headband. In some instances, the headband may inadvertently be worn back-to-front, resulting in misplacement of the electrodes.

Poor connection to skin. Electrodes may not be sufficiently connected to the user's skin to give a clear EEG reading, for example due to sweating.

Changes in the ambient electrical fields may manifest as artifacts in EEG readings.

Muscle movements in forehead, jaw and eyelids may reduce signal quality of EEG.

Inter-personal variance. EEG patterns vary from person to person. For example, elderly users show substantially different EEG patterns to those of the younger population. These differences may be included in historic EEG signals, to give great context.

For other categories of physiological signals, the same inaccuracy sources may apply. Each inaccuracy source may itself have a characteristic effect on physiological signals. Therefore, it may be possible to classify sleep states associated with lower reliability values, based on the characteristics of the received physiological signals. Therefore, the reliability value may be correspondingly raised. In a further example, manual identification of the source of the inaccuracy may be performed and an indication of the identified inaccuracy source may be included in the historic physiological signals. Therefore, identification of the sleep state may be possible for physiological signals which would otherwise be deemed too uncertain to result in reliable sleep state categorization.

Figure 2:
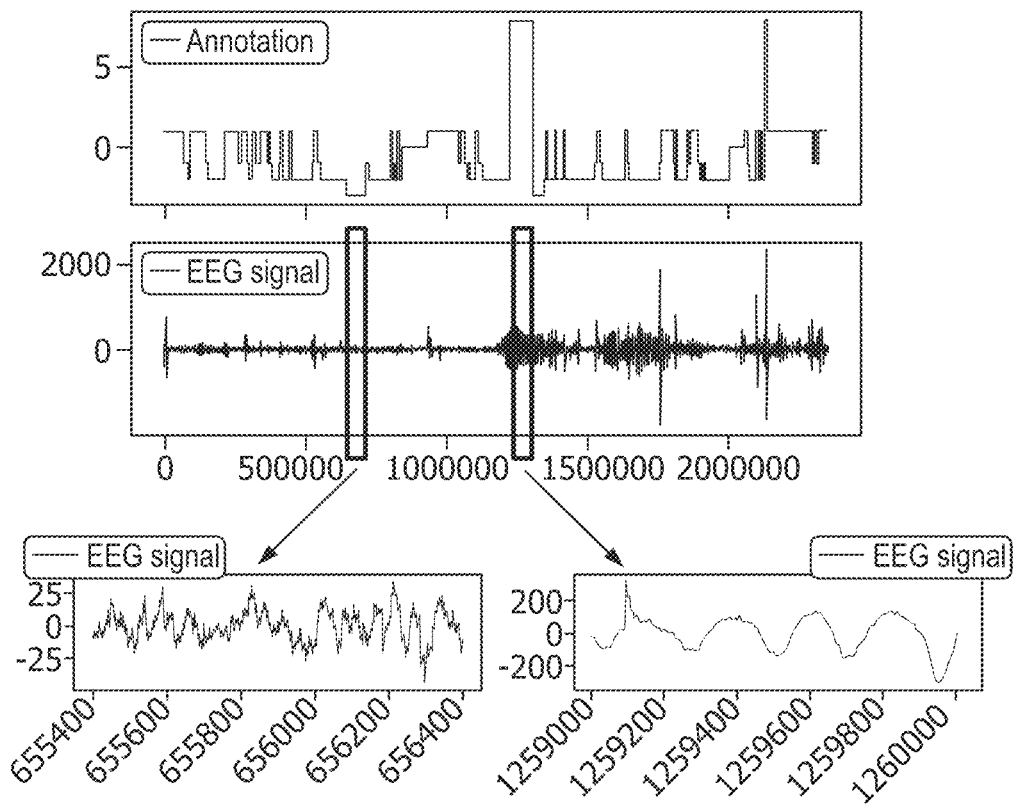
FIG. 2 is an example of an EEG signal and signal annotation.

FIG. 2 shows an example of an EEG signal, along with an annotation of the signal to place each sleep period into a category corresponding to a sleep state or to identify the period as corrupted and therefore cannot be given a categorization. In FIG. 2, numbers are assigned to the various sleep states or other categories in the annotation of the signal. In this case, −3 is NREM stage 3, −2 is NREM stage 2, −1 is NREM stage 1, 0 is REM sleep, 1 is awake and 8 is corrupted. This is just one example of a way of annotating an EEG signal.

FIG. 2 shows an expanded view of two 10 second periods from the EEG signal. In the first expanded view, between the times 655400 and 656400, a normal EEG signal of a deep (stage 3) NREM sleep is shown. This EEG signal would be easily categorized with a high reliability value. In the second expanded view, between the times 1259000 and 1260000, a corrupted EEG signal is shown. This signal would have a low reliability value, and potentially low enough that a sleep state may not be assigned. However, based on historic EEG signals, similar patterns may have been observed in the past and categorized into a sleep state such that the reliability is raised and the period can be assigned a sleep state.

Figure 3:
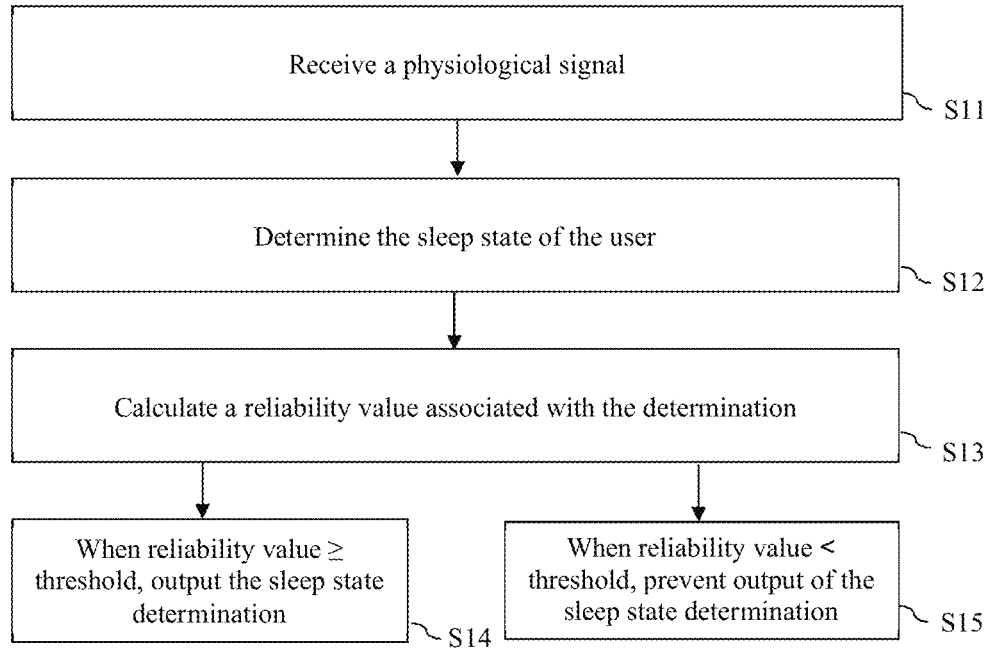
FIG. 3 is another flowchart of an example of a method in accordance with an embodiment.

In some examples, as shown in FIG. 3, the method may further comprise outputting S14 the sleep state determination when the reliability value is equal to or higher than a predetermined first threshold value. In other words, a threshold value may be set, above which the reliability is deemed high enough that useful sleep state determination can be achieved. As shown in FIG. 3, the method may further comprise preventing S15 output of the sleep state determination when the reliability value is lower than the predetermined first threshold value. Therefore, if the threshold level of reliability is not met, useful sleep state determination is deemed not possible and a sleep state category is not output. In this case either no categorization may be output or a determination indicating no category may be output. Further action may be taken based on the output sleep state determination or determination indicating no category. This is discussed in more detail below. Reliability values may for example be given in the form of a number from 1 to 10, with 1 being the least reliable and 10 being the most reliable. The first threshold value may for example be set at 2.

Figure 4:
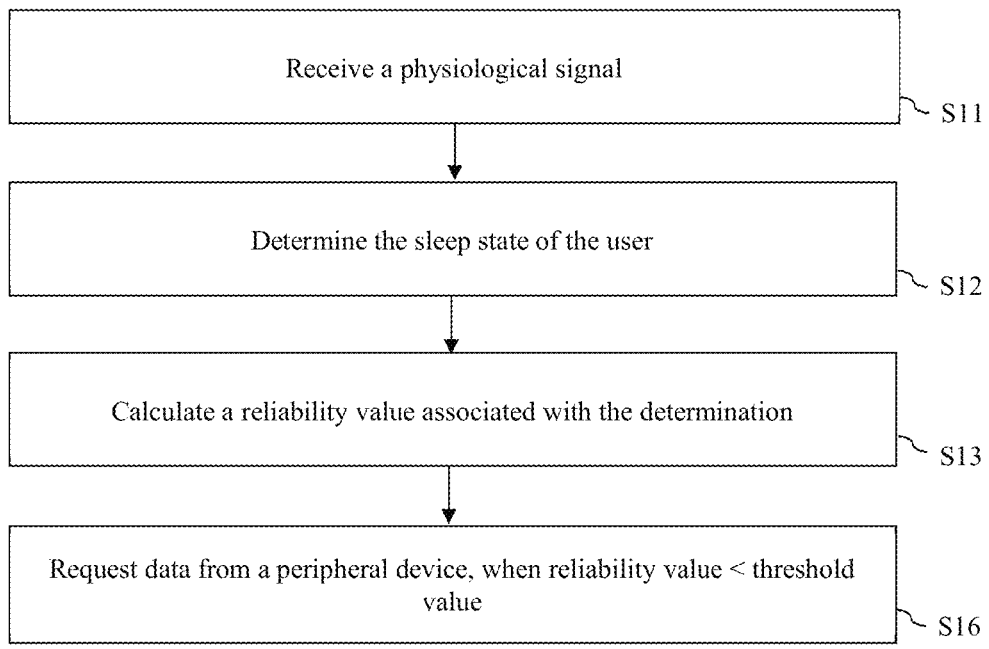
FIG. 4 is another flowchart of an example of a method in accordance with an embodiment.

In some examples, as shown in FIG. 4, the method may further comprise requesting S16 data from a peripheral device when the reliability value is lower than a second predetermined threshold value. A second threshold value may be set indicating that reliability is not so low that the physiological signal cannot be categorized, but is low enough that the categorization may be improved with more information. Therefore, the threshold may be set higher than the first threshold value. That is to say, the second threshold is associated with a higher level of reliability than the first threshold value. The second threshold value, on the scale detailed above, may for example be set at 3.

The peripheral device may for example be a wearable device or any other sleep monitoring device. Correlation between data collected from the peripheral device and the physiological signal may improve reliability when determining a category for a period of the physiological signal.

In some examples, peripheral devices include any of an inertia sensor, a temperature sensor, a strain sensor and a skin conductance sensor. Each peripheral device may produce one or more types of sleep monitoring data or associated data useful for putting the received physiological signals into context in order to improve the reliability value. For example, an inertia sensor may detect movement of a user. Movement may affect the physiological signal, for example if it were to include EEG signals, but may also be associated with some sleep states and not others. Therefore, it may be useful to correlate this data with the received physiological signal, for a particular time period, in order to improve the reliability associated with a sleep state determination for that time period. In another example, a user's temperature may fluctuate during sleep and such fluctuations may be indicative of a sleep state. Further, electrodes used to detect an EEG signal of a user may have attached thereto a strain sensor to detect when the electrodes, or other parts of the device to which the electrodes are attached, are under strain. Further still, a skin conductance sensor may give an indication of perspiration, which may affect an EEG signal depending on the level of conductance detected. Correlation of data collected from any one or more peripheral devices may be used to increase the reliability value associated with a sleep state determination for a particular time period.

In some examples, the determining is performed by a neural network. The neural network may for example be a deep neural network and the neural network architecture may include convolutional layers, or recurrent layers (for example long short-term memory, LSTM, layer blocks). The output layer of the neural network may generate the sleep state determination and may further generate an associated reliability value. The output layer of the neural network may use for example a SoftMax activation.

Figure 5:
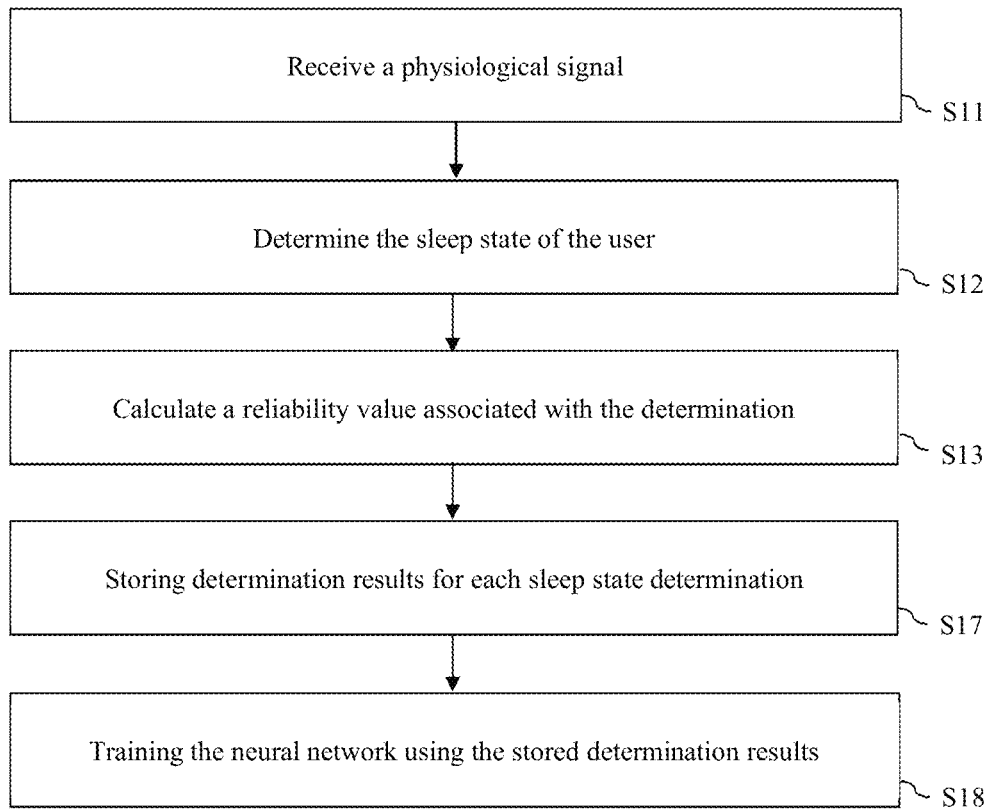
FIG. 5 is another flowchart of an example of a method in accordance with an embodiment.

In some examples, as shown in FIG. 5, the method may further comprise storing S17 determination results for each sleep state determination. The determination results may be stored in any suitable memory. Determination results may be stored including associated reliability values, or other associated data or metadata. In this way, a database of determination results may be built up, which may yield more accurate sleep state determination, as the number of stored results grows. The method may further comprise training S18 the neural network using the stored determination results.

The neural network output may be generated by imposing a similar threshold on the values of the output layer. If the physiological signal deviates too far from an expected range, or a reliability value for a particular time period is lower than a threshold, then the neural network does not output a sleep state determination for the time period. The neural network may further use Bayesian Deep Learning methods like Monte Carlo dropout to generate the reliability estimate along with the sleep state determination for the specific time period. The neural network may further use out-of-distribution analysis methods to improve accuracy of the determination.

According to the processing performed by the neural network a temporal model uncertainty function of $u_m(t)$ may be produced, which in a typical embodiment is a vector values signal of multiple uncertainty metrics. As set out above, peripheral devices, such as sensors may provide further data for processing by the neural network. Such sensors may, for example, include inertial sensors, skin temperature sensors, or strain sensors. Strain sensors may for example be included in a headband strap holding electrodes to a user's head, from which EEG signals may be detected, and skin conductance measurements may be taken between the EEG electrodes.

Based on the processing and further sensor signals, a detection model may be developed for all conditions for the sources of signal deterioration. The detection models may typically be based on neural networks. The outcomes of all sensor measurements, including the EEG signal detector, are collected in a time-varying vector-valued sensor uncertainty function $u_s(t)$.

In an example the final uncertainty $U(t)$ is an inner product of the combined vector signals of $u(t)=[u_m(t), u_s(t)]$ and a weight vector of w so that:

$$U(t) = w^T u(t)$$

The weight of w may be designed in advance and included in the program code or it may be possible to learn it over time, based on system performance and feedback from the user. The uncertainty function may represent the inverse of a reliability value, such that the higher the uncertainty, the lower the reliability.

In an embodiment of a further example a causal inference technique may be used to estimate the causal relation of different environmental conditions to the certainty of the staging model in a particular user over time in different conditions, and optimize the weight w to maximize the reliable determination of the user sleep state, based on the detected signals and data collected from peripheral devices.

Figure 6:
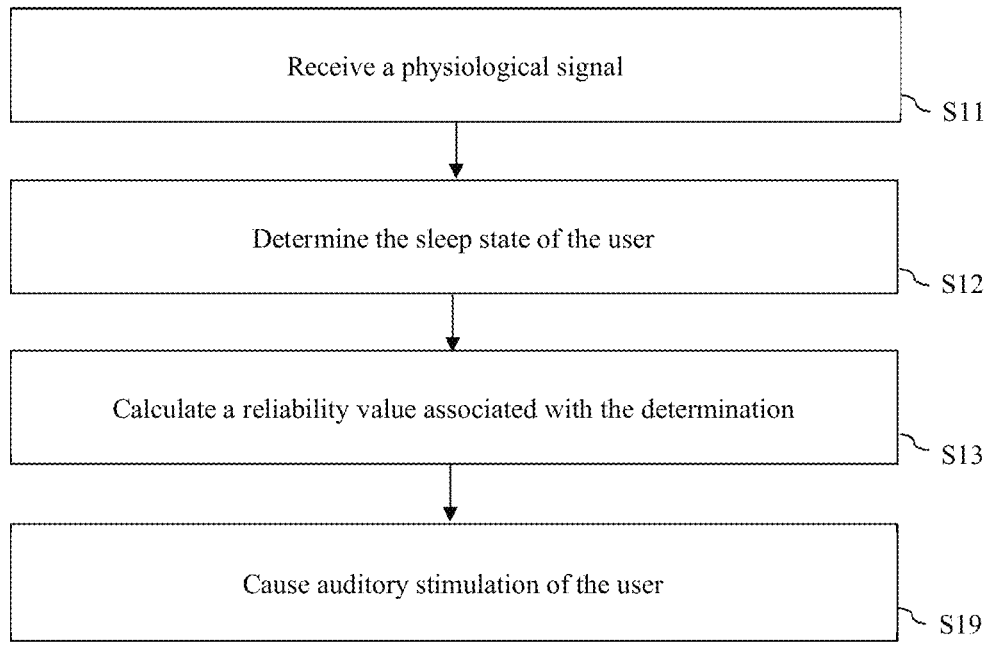
FIG. 6 is another flowchart of an example of a method in accordance with an embodiment.

In some examples, as shown in FIG. 6, the method may further comprise causing S19 auditory stimulation of the user, based on the output sleep state determination. Auditory stimulation, when applied during the appropriate sleep state, and without disturbing the user's sleep or waking them up, may enhance sleep's restorative effects. For example, initiating auditory stimulation of the user when it is determined that the user is in stage 3 NREM sleep, may help the user to feel more rested the following day. In further examples, stimulation may include outputs other than auditory stimulation, such as haptic stimulation of the user, for example.

In some examples, the method detailed above may be carried out by a program, which may be stored on any suitable storage medium, such that when the program is executed on a suitable computer processor, a process is carried out according to the method. Further, the method may be performed on any suitable device, an example of which is detailed below.

Figure 7:
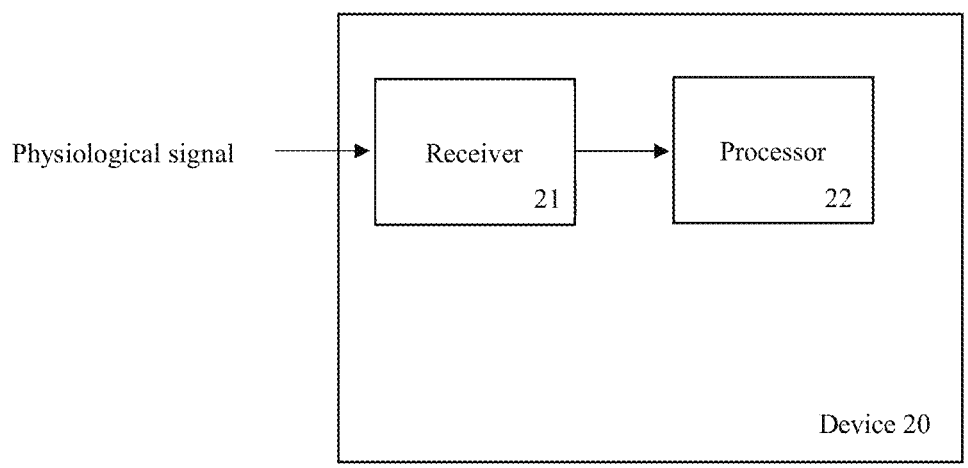
FIG. 7 is a simplified schematic of an example of a device in accordance with an embodiment.

In an example, as shown in FIG. 7, there is provided an embodiment of a device 20 for determining a sleep state of a user. The device 20 comprises a receiver 21 to receive a physiological signal from a physiological signal detector used by the user. The device 20 further comprises a processor 22 to determine, based on the received physiological signal, the sleep state of the user and calculate a reliability value associated with the determination. The reliability value being calculated based on a comparison of the received physiological signal with historic physiological signals of the same sleep state as the determined sleep state.

The physiological signal detector may for example be separate from the device 20, or included in the device 20. The physiological signal detector may in one example be an EEG signal detector and may include electrodes to attach to the user. The device 20 may for example be a wearable device, such as a headband in which such electrodes are included. The processor 22 may be any suitable computing device. The reliability value may for example be used as a weight, to give the associated determined sleep state a relative significance to other determined sleep states in the historic physiological signals. In this way, historic physiological signals with low variation from the expected signals for a given sleep state may be given a higher reliability value and as such, may be used to improve the understanding of what an expected signal is. Higher variation from expected signals may lead to a lower reliability value, meaning associated signals may be given a lower relative significance when developing what an expected signal is. In this way, the reliability value may be considered as a metric for improving the immediate sleep state determination, but may also be used to improve future determinations.

The processor 22 may further output the sleep state determination when the reliability value is equal to or higher than a first threshold value. The processor 22 may for example prevent output of the sleep state determination when the reliability value is lower than the first threshold value. In an example, sleep state determinations and the physiological signals from which they are determined, which have a reliability value below the first threshold value may be excluded from the historic physiological signals used for future determinations.

In some examples, the processor 22 may further request data from a peripheral device when the reliability value is lower than a second threshold value. Data from the peripheral device may be correlated with the received physiological signals in order to give further context to the physiological signals for the purpose of sleep state determination. If, as a result of such correlation, a sleep state may be more reliably determined, the reliability value may be updated as appropriate, which may raise the reliability value to above the second threshold value. Examples of a peripheral device may include any of an inertia sensor, a temperature sensor, a strain sensor, a skin conductance sensor or any other device providing information or data relating to the sleeping or waking state of a user.

Figure 8:
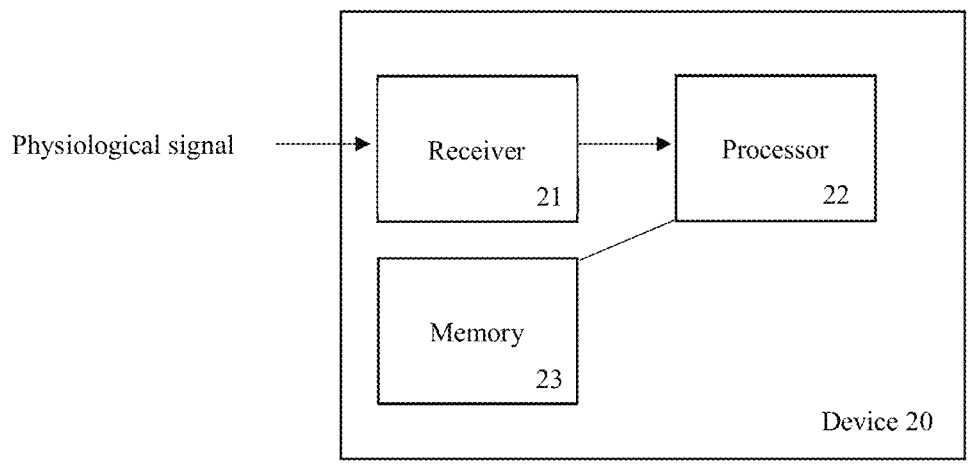
FIG. 8 is another simplified schematic of an example of a device in accordance with an embodiment.

In an example, as shown in FIG. 8, the device 20 may further comprise a memory 23 to store determination results for each sleep state determination. The memory 23 may be any suitable memory for storing determination results, historic physiological signals, reliability values and any other data or metadata useful for future sleep state determination. The processor 22 may comprise a neural network to determine the sleep state of the user and the neural network is trained using the stored determination results.

Figure 9:
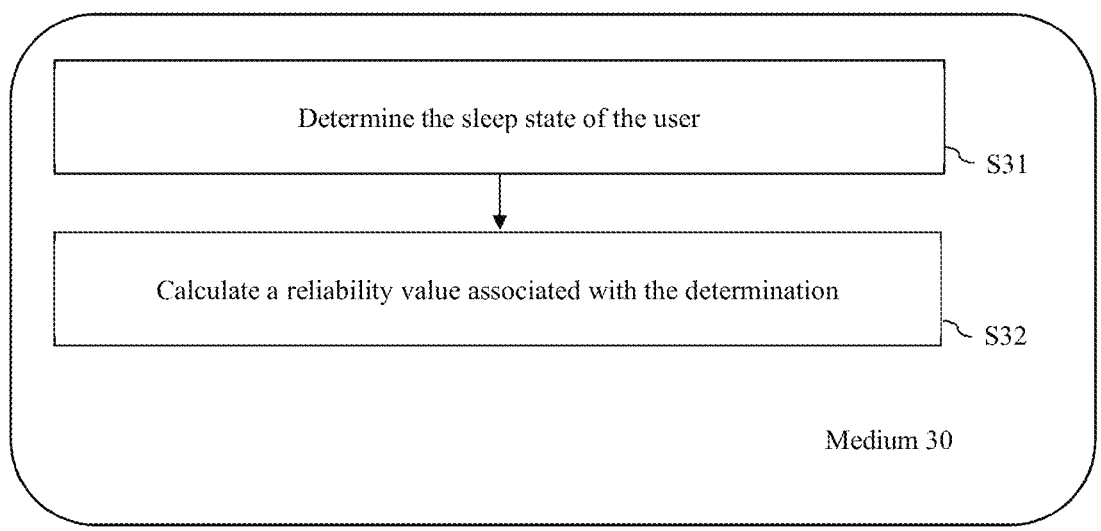
FIG. 9 is an example of a medium in accordance with an embodiment.

In an example, as shown in FIG. 9, there is provided an embodiment of a non-transitory computer-readable medium 30 storing a program which, when executed on a computer, is configured to cause the computer to perform a process. The process comprises determining S31, based on a received physiological signal received from a physiological signal detector used by a user, the sleep state of the user. The process further comprises calculating S32 a reliability value associated with the determination, the reliability value being calculated based on a comparison of the received physiological signal with historic physiological signals of the same sleep state as the determined sleep state.

The process may further comprise storing determination results for each sleep state determination and training a neural network using the stored determination results, as set out in detail above. The process may further comprise requesting data from a peripheral device when the reliability value is lower than a threshold value, as set out in relation to the method and device above.

Examples in the present disclosure can be provided as methods, systems or machine readable instructions, such as any combination of software, hardware, firmware or the like. Such machine readable instructions may be included on a computer readable storage medium (including but is not limited to disc storage, CD-ROM, optical storage, etc.) having computer readable program codes therein or thereon.

The present disclosure is described with reference to flow charts and block diagrams of the method, devices and media according to examples of the present disclosure. Although the flow diagrams described above show a specific order of execution, the order of execution may differ from that which is depicted. Blocks described in relation to one flow chart may be combined with those of another flow chart. It shall be understood that each flow and block in the flow charts and block diagrams, as well as combinations of the flows and diagrams in the flow charts and block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing apparatus may execute the machine readable instructions. Thus functional modules of the apparatus and devices may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by flow(s) in the flow charts or block(s) in the block diagrams.

Further, the teachings herein may be implemented in the form of a computer software product, the computer software product being stored in a storage medium and comprising a plurality of instructions for making a computer device implement the methods recited in the examples of the present disclosure.

The features of any dependent claim may be combined with the features of any of the independent claims or other dependent claims.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for determining a sleep state of a user in a system that includes one or more physiological sensors comprising one or more of a polysomnogram (PSG) sensor, an electroencephalogram (EEG) sensor, or an electrocardiogram (ECG) sensor, one or more peripheral devices comprising one or more of an inertia sensor, a temperature sensor, a strain sensor or a skin conductance sensor, and a processor configured to implement a deep neural network having a plurality of layers comprising convolutional layers or recurrent layers, an output layer, and a detection model developed for detection of conditions or sources of signal detection in signals generated by the one or more physiological sensors that employs a time-varying vector-valued sensor uncertainty function, the method comprising:

receiving one or more physiological signals from the one or more physiological sensors used by the user;

determining the sleep state of the user based on the received one or more physiological signals and without data from the one or more peripheral sensors using the deep neural network, wherein the output layer generates the determined sleep state using a softmax function;

calculating a reliability value indicative of a reliability of the determination of the sleep state using the deep neural network based on the received one or more physiological signals and without an output from the one or more peripheral sensors, the reliability value being calculated based on a comparison of the received one or more physiological signals with one or more historic physiological signals each associated with a historic user and a historic sleep state previously determined for the historic user that is the same as the determined sleep state, wherein the output layer generates the reliability value using the softmax function and a Bayesian deep leaning method;

responsive to determining that the reliability value is lower than a first threshold value, preventing output of the sleep state determination;

responsive to determining that the reliability value is greater than a second threshold value that is greater than the first threshold value, outputting the sleep state determination; and responsive to determining that the first reliability value is greater than or equal to the first threshold value and less than the second threshold value, requesting and receiving data from the one or more peripheral devices, determining an updated sleep state of the user and an updated reliability value for the updated sleep state using the detection model and the time-varying vector-valued sensor uncertainty function of the deep neural network based on the received one or more physiological signals and the received data from the one or more peripheral devices, and outputting the updated sleep state determination only if the updated reliability value is greater than the second threshold value.

2. The method according to claim 1, further comprising storing determination results for the sleep state determination or the updated sleep state determination and training the neural network using the stored determination results.

3. The method according to claim 1, further comprising causing auditory stimulation of the user based on the sleep state determination.

4. A system for determining a sleep state of a user, comprising:
one or more physiological sensors comprising one or more of a polysomnogram (PSG) sensor, an electroencephalogram (EEG) sensor, or an electrocardiogram (ECG) sensor;
one or more peripheral devices comprising one or more of an inertia sensor, a temperature sensor, a strain sensor or a skin conductance sensor; and
a processor configured to implement a deep neural network having a plurality of layers comprising convolutional layers or recurrent layers, an output layer, and a detection model developed for detection of conditions or sources of signal detection in signals generated by the one or more physiological sensors that employs a time-varying vector-valued sensor uncertainty function, the processor being further configured to:
receive one or more physiological signals from the one or more physiological sensors used by the user;
determine the sleep state of the user based on the received one or more physiological signals and without data from the one or more peripheral sensors using the deep neural network, wherein the output layer generates the determined sleep state using a softmax function;
calculate a reliability value indicative of a reliability of the determination of the sleep state using the deep neural network based on the received one or more physiological signals and without an output from the one or more peripheral sensors, the reliability value being calculated based on a comparison of the received one or more physiological signals with one or more historic physiological signals each associated with a historic user and a historic sleep state previously determined for the historic user that is the same as the determined sleep state, wherein the output layer generates the reliability value using the softmax function and a Bayesian deep leaning method;
determine whether the reliability value is lower than a first threshold value;
responsive to determining that the reliability value is lower than the first threshold value, prevent output of the sleep state determination;
determine whether the reliability value is greater than a second threshold value that is greater than the first threshold value;
responsive to determining that the reliability value is greater than a second threshold value, output the sleep state determination; and
determine whether the first reliability value is greater than or equal to the first threshold value and less than the second threshold value;
responsive to determining that the first reliability value is greater than or equal to the first threshold value and less than the second threshold value, request and receive data from the one or more peripheral devices, determine an updated sleep state of the user and an updated reliability value for the updated sleep state using the detection model and the time-varying vector-valued sensor uncertainty function of the deep neural network based on the received one or more physiological signals and the received data from the one or more peripheral devices, and output the updated sleep state determination only if the updated reliability value is greater than the second threshold value.

5. The system according to claim 4, wherein the processor is adapted to store determination results for the sleep state determination or the updated sleep state determination and train the neural network using the stored determination results.

6. A non-transitory computer-readable medium storing a program which, when executed on a computer, is configured to cause the computer to perform a method according to claim 1 in a system according to claim 1.

* * * * *